(12) United States Patent
Ikenoue et al.

(10) Patent No.: US 7,807,663 B2
(45) Date of Patent: Oct. 5, 2010

(54) THERAPEUTIC AGENTS FOR DIABETES

(75) Inventors: Takao Ikenoue, Kawasaki (JP); Yoko Kageyama, Kawasaki (JP); Yukio Iino, Kawasaki (JP); Nobuo Kondo, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/198,511

(22) Filed: Aug. 8, 2005

(65) Prior Publication Data

US 2005/0272641 A1 Dec. 8, 2005

Related U.S. Application Data

(63) Continuation of application No. PCT/JP2004/001279, filed on Feb. 6, 2004.

(30) Foreign Application Priority Data

Feb. 7, 2003 (JP) .............................. 2003-031088

(51) Int. Cl.
| A61K 31/553 | (2006.01) |
| A61K 31/55 | (2006.01) |
| A61K 31/175 | (2006.01) |
| A61K 31/155 | (2006.01) |

(52) U.S. Cl. .................. 514/211.11; 514/220; 514/592; 514/635; 514/866

(58) Field of Classification Search ............ 514/211.11, 514/220, 35, 634, 635, 866, 909, 592
See application file for complete search history.

(56) References Cited

U.S. PATENT DOCUMENTS

| 2,961,377 | A | * | 11/1960 | Shapiro et al. | ............... | 514/635 |
| 3,174,901 | A | * | 3/1965 | Sterne | ........................ | 514/635 |
| 3,501,495 | A | * | 3/1970 | Laszlo et al. | ................. | 548/515 |
| 4,062,950 | A | * | 12/1977 | Frommer et al. | .............. | 514/35 |
| 2004/0048847 | A1 | | 3/2004 | Iino et al. | | |

FOREIGN PATENT DOCUMENTS

| WO | WO 02/44180 A1 | 8/2002 |
| WO | WO 2005/042536 A1 | 5/2005 |

OTHER PUBLICATIONS

Windholz et al., The Merck Index, Tenth Edition, 1983, p. 3, abstract No. 11 and p. 204, abstract No. 1445.*
Leibowitz et al., "A novel insulin secretagogue is a phosphodiesterase inhibitor", Diabetes, vol. 44, issue 1, pp. 67-74 (abstract).*
U.S. Appl. No. 11/486,213, filed Jul. 14, 2006, Hirama, et al.
M.D., Mashkovsky, "Medicaments", Moscow Medicine, 1985, part 1, pp. 551-552, 562-563 (with English translation).
M. Riddle, "Combining Sulfonylureas and Other Oral Agents", The American Journal of Medicine, vol. 108, 6A, Apr. 17, 2000, pp. 15S-22S.
J. Buse, "Combining Insulin and Oral Agents", The American Journal of Medicine, vol. 108, 6A, Apr. 17, 2000, pp. 23S-32S.
H. Gin, et al., "Oral Anti Diabetic Polychemotherapy in Type 2 Diabetes Mellitus", Diabetes Metab, vol. 28, No. 5, 2002, pp. 350-353.
M. Okubo, et al., "Pharmacologic Profile of Oral Antidiabetic Agents", Nippon Rinsho, 60 Suppl, 9, pp. 310-316 w/attached English excerpt, (2002).
U.S. Appl. No. 11/398,675, filed Apr. 6, 2006, Iino, et al.
U.S. Appl. No. 11/414,499, filed May 1, 2006, Hirama, et al.

* cited by examiner

*Primary Examiner*—Kevin Weddington
(74) *Attorney, Agent, or Firm*—Oblon, Spivak, McClelland, Maier & Neustadt, L.L.P.

(57) ABSTRACT

A pharmaceutical composition for preventing and/or treating diabetes, diabetic complication, hyperinsulinemia, disorders of glucose metabolism or obesity, comprising a combination of the following compound, analogues or pharmaceutically acceptable salts thereof with a hypoglycemic agent.

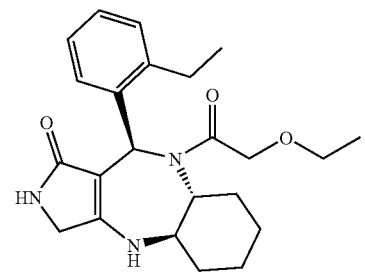

39 Claims, 2 Drawing Sheets

THERAPEUTIC AGENTS FOR DIABETES

BACKGROUND OF THE INVENTION

The present invention relates to new agents for preventing/treating diabetes, more concretely pharmaceutical compositions comprising a combination of a compound represented by the following formula (I) with a specified medicament(s), and particularly drugs for preventing or treating diabetes.

Diabetes is metabolic disorders caused by an absolute or a relative shortage of insulin that is only hypoglycemic hormone, and has a main feature of continuous hyperglycemia. The continuity of hyperglycemic status not only makes the metabolic disorders caused by a shortage of insulin worse but also causes microangiopathy in a kidney, nerves, retinas, and the like; and macroangiopathy such as arteriosclerosis. As a result, such a status seriously spoils a healthy life. Therefore, the object of controlling diabetes is to prevent the occurrence of the chronic complication and slow the progression thereof by improving the hyperglycemic status.

Hypoglycemic agents such as insulin preparations, insulin secretagogues, insulin sensitizers and α-glucosidase inhibitors have been widely applied as the method for the clinical treatment. Each of these hypoglycemic agents has many problems though the availability of such agents has been confirmed. For example, in the case of the diabetic patients whose pancreatic insulin secretion ability seriously lowers, effectiveness of insulin secretagogues and insulin sensitizers is diminished. Similarly, in the case of the diabetic patients whose insulin resistance is significantly high, effectiveness of insulin preparations and insulin secretagogues is diminished.

It is thought to be useful that agents having different action mechanisms are combined to use in order to complement the above disadvantages of the hypoglycemic agents. However, the use of the combination of the existing hypoglycemic agents has a limitation in improving the hyperglycemic status in point of corresponding to various pathology of diabetes.

As one of the main actions of insulin relating to the hypoglycemic actions, insulin has the action which reinforces the sugar transportation ability of peripheral cells and, as a result, lowers the blood glucose level. The compound of the formula (I) described in the patent application (WO02/44180) according to the present applicant has the effect of reinforcing the sugar transportation and is useful for treating the diabetic patients. Namely, the compound of the formula (I) is the compound which lowers the blood glucose level by reinforcing the sugar transportation activity of the peripheral cells, and can be oral administered agents having a new action mechanism.

Further, though the effect of reinforcing the sugar transportation of the compound of the formula (I) has been described in the patent application (WO02/44180), the combinational effect thereof with the other agent(s) has not been described.

DISCLOSURE OF THE INVENTION

The object of the present invention is, for example, to provide pharmaceutical compositions that can be used as excellent agents for preventing/treating diabetes, particularly those having a high improvement effect on hyperglycemia, which cannot be obtained by using the conventional hypoglycemic agents.

In order to solve the above problems, the inventors have thoroughly studied and found that when a compound represented by the following formula (I) is combined with at least one kind of an agent selected from following Group A to use, a remarkable therapeutic effect on antidiabetic actions, especially the hypoglycemic action can be obtained as compared with the use of the compounds separately without combination thereof. The present invention has been completed based on these findings.

Namely, the present invention provides pharmaceutical compositions comprising a combination of a compound represented by the following formula (I) or pharmaceutically acceptable salts thereof and at least one kind of an agent selected from following Group A:

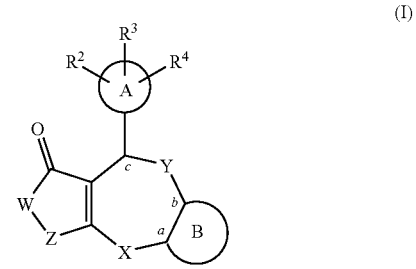

(I)

wherein Ring A represents an aromatic ring, a heterocyclic ring or an aliphatic ring; $R^2$, $R^3$ and $R^4$ may be same or different from each other and each independently represents a hydrogen atom, a halogen atom, a hydroxy group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, a trifluoromethyl group, an aryl group which may have a substituent(s), a heteroaryl group which may have a substituent(s), a benzyloxy group which may have a substituent(s), an aryloxy group which may have a substituent(s), a heteroaryloxy group which may have a substituent(s), an arylamino group which may have a substituent(s), an arylvinyl group which may have a substituent(s) or an arylethynyl group which may have a substituent(s); Ring B represents an aromatic ring which may have a substituent(s), a heterocyclic ring which may have a substituent(s) or an aliphatic ring which may have a substituent(s); —X—, —Y— and -Z- may be same or different from each other and each independently represents —O—, —NH—, —NR$^5$—, —S—, —SO—, —SO$_2$—, —CH$_2$—, —CR$^6$R$^7$— or —CO— wherein R$^5$ represents a lower alkyl group which may have a substituent(s), an acyl group which may have a substituent(s), an alkoxycarbonyl group which may have a substituent(s), a carbamoyl group which may have a substituent(s) or a sulfonyl group which may have a substituent(s), $R^6$ and $R^7$ may be same or different from each other and each independently represents a hydrogen atom, a halogen atom, a hydroxy group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group or a trifluoromethyl group; —W— represents —NR$^1$—, —O— or —CR$^8$R$^9$—, wherein $R^1$ represents a hydrogen atom, a lower alkyl group which may have a substituent(s) or an aryl group which may have a substituent(s), $R^8$ and $R^9$ may be same or different from each other and each independently represents a hydrogen atom, a halogen atom, a hydroxy group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group or a trifluoromethyl group; and a, b and c represents a position of a carbon atom, respectively; with the proviso that the above substituent(s) is selected from the group consisting of a halogen atom, a hydroxy group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group, a trifluoromethyl group, an aryl group and a heteroaryl group. Group A: insulin preparations, insulin derivatives, insulin-like agonists, insulin secretagogues, insulin sensitizers, biguanides, gluconeogenesis inhibitors, sugar absorption inhibitors, renal sugar re-uptake inhibitors, β3 adrenergic receptor agonists, glucagon-like peptide-1, analogues of glucagon-like peptide-1, glucagon-like peptide-1 receptor agonists, dipeptidyl peptidase IV inhibitors, aldose reductase inhibitors, advanced glycation endproducts production inhibitors, glycogen synthase kinase-3 inhibitors, glycogen phosphorylase inhibitors, antilipemic agents, anorexic agents, lipase inhibitors, antihypertensive agents, peripheral circulation improving agents, antioxidants, diabetic neuropathy therapeutic agents.

The present invention also provides the above pharmaceutical compositions for preventing and/or treating diseases caused by hyperglycemia.

Further, the present invention provides the above pharmaceutical compositions for preventing and/or treating diabetes, diabetic complication, hyperinsulinemia, glucose intolerance or obesity.

BEST MODE FOR CARRYING OUT THE INVENTION

Figure 1:
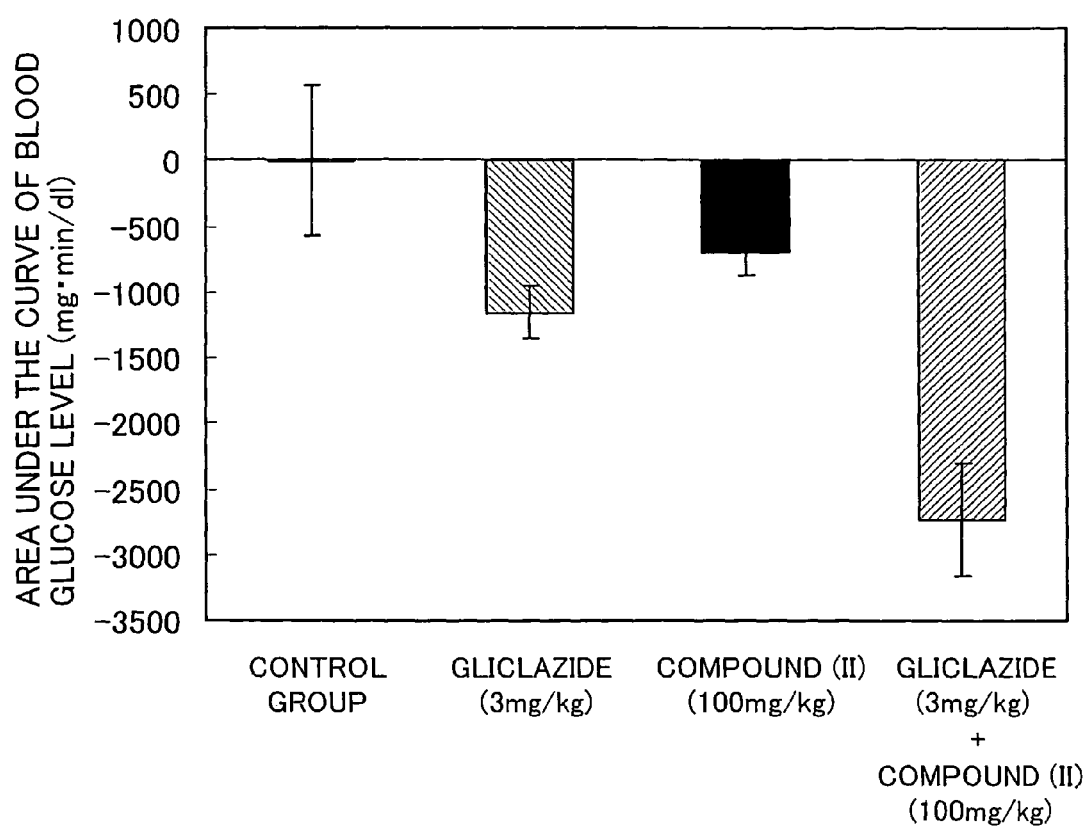
FIG. 1 is a chart showing a combinational effect of the compound (II) and gliclazide in Example 1 (average value±standard deviation, each group N=4).
Figure 2:
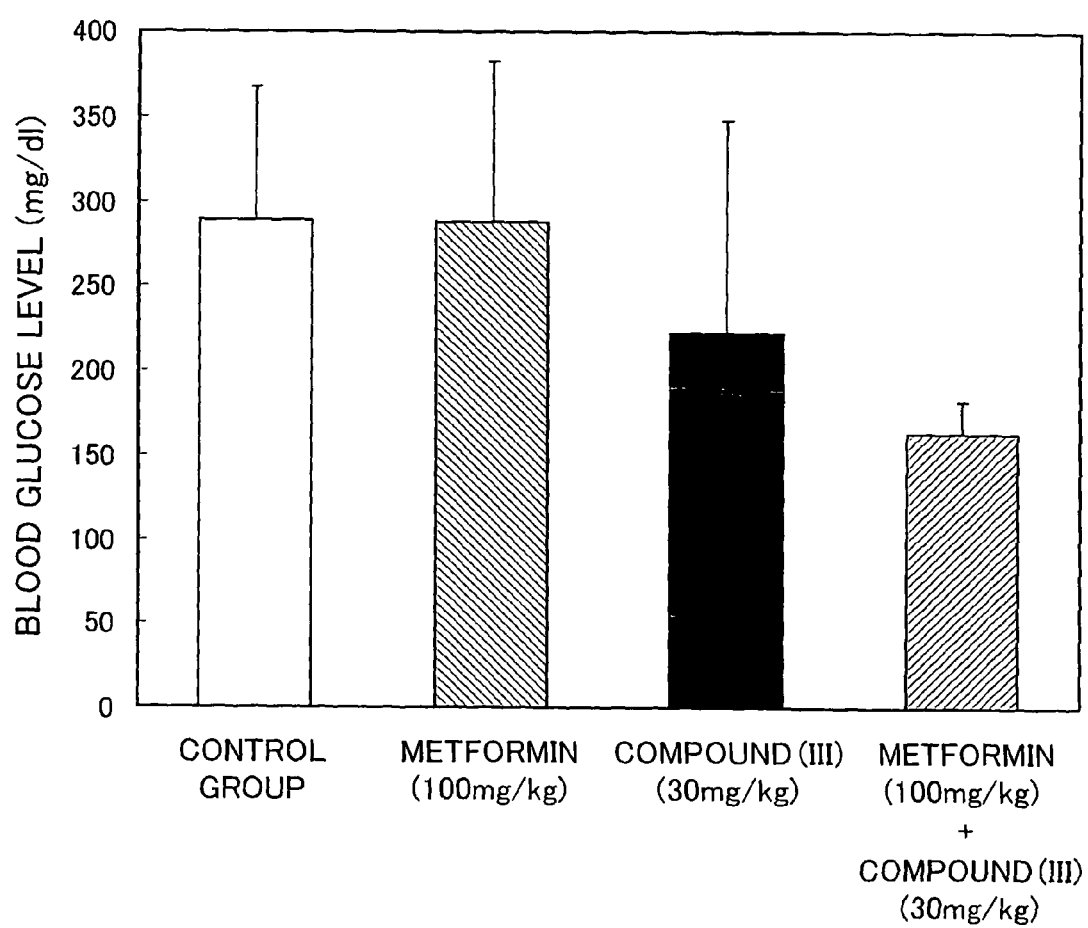
FIG. 2 is a chart showing a combinational effect of the compound (III) and metformin in Example 3 (average value+ standard deviation, each group N=6).

The pharmaceutical compositions of the present invention are those combining the compound of the formula (I) and at least one kind of an agent selected from above Group A (namely, combined agents), and conformation thereof may be of any form if only the compound of the formula (I) can be combined with at least one kind of an agent selected from above Group A when administered. Therefore, the agents for preventing/treating diabetes of the present invention may be a single drug product obtained by preparing the compound of the formula (I) and at least one kind of an agent selected from above Group A at one time, or combined products consisting of at least two kinds of drug products obtained by separately preparing the compound of the formula (I) and at least one kind of an agent selected from above Group A.

In the present invention, the compound of the formula (I) is orally administered agents having the above-mentioned effect of reinforcing the sugar transportation, useful for the treatment of the diabetic patents, lowering the blood glucose level by reinforcing the sugar transportation ability of peripheral cells and having a new action mechanism to diabetes. The definitions of each of the symbols in the compound of the formula (I) are mentioned above, and a lower alkyl group and the like shown in each of the symbols can be defined as follows.

A lower alkyl group represents a linear- or branched-chain or cyclic alkyl group having 1 to 6 carbon atoms. For example, it includes a methyl group, an ethyl group, n-propyl group, n-butyl group, n-pentyl group, n-hexyl group, an isopropyl group, an isobutyl group, sec-butyl group, tert-butyl group, an isopentyl group, tert-pentyl group, neopentyl group, 2-pentyl group, 3-pentyl group, n-hexyl group, 2-hexyl group, a cyclopropyl group, cyclobutyl group, cyclopentyl group and cyclohexyl group. An alkyl group having 1 to 3 carbon atoms is preferred and particularly preferred are a methyl group, an ethyl group and the like.

An aryl group represents a mono- or bi-cyclic aromatic substituent(s) composed of 6 to 13 carbon atoms. Examples thereof are a phenyl group, an indenyl group, a naphthyl group and a fluorenyl group, and a phenyl group is preferred.

A halogen atom includes a fluorine atom, a chlorine atom, a bromine atom and an iodine atom.

An alkyl group represents a linear- or branched-chain or cyclic alkyl group having 1 to 18 carbon atoms. For example, it includes a methyl group, an ethyl group, n-propyl group, n-butyl group, n-pentyl group, n-hexyl group, n-heptyl group, n-octyl group, n-nonyl group, n-decyl group, n-undecyl group, n-dodecyl group, an isopropyl group, an isobutyl group, sec-butyl group, tert-butyl group, an isopentyl group, tert-pentyl group, neopentyl group, 2-pentyl group, 3-pentyl group, n-hexyl group, 2-hexyl group, tert-octyl group, a cyclopropyl group, cyclobutyl group, cyclopentyl group, cyclohexyl group and 1-adamantyl group. An n-hexyl group, n-heptyl group, n-octyl group, n-nonyl group, n-decyl group, n-undecyl group, n-dodecyl group, an isopropyl group, an isobutyl group, sec-butyl group, tert-butyl group, an isopentyl group, tert-pentyl group, neopentyl group, 2-pentyl group, 3-pentyl group, n-hexyl group, 2-hexyl group, tert-octyl group, cyclopropyl group, cyclobutyl group, cyclopentyl group, cyclohexyl group, 1-adamantyl group and the like are preferred, and an isopropyl group, tert-butyl group, tert-octyl group, 1-adamantyl group and the like are more preferred.

An alkoxy group represents an alkoxy group which has a linear- or branched-chain or cyclic alkyl group having 1 to 18 carbon atoms. For example, it includes a methoxy group, an ethoxy group, n-propoxy group, n-butoxy group, n-pentyloxy group, n-hexyloxy group, n-heptyloxy group, n-octyloxy group, n-nonyloxy group, n-decyloxy group, n-undecyloxy group, n-dodecyloxy group, an isopropoxy group, an isobutoxy group, sec-butoxy group, tert-butoxy group, a cyclopropyloxy group, a cyclobutoxy group, a cyclopentyloxy group, a cyclohexyloxy group, cycloheptyloxy group, 2-cyclohexylethoxy group, 1-adamantyloxy group, 2-adamantyloxy group, 1-adamantylmethyloxy group, 2-(1-adamantyl)ethyloxy group and a trifluoromethoxy group. Among them, a methoxy group, an ethoxy group, n-propoxy group, an isopropoxy group, n-butoxy group, tert-butoxy group, n-pentyloxy group and n-hexyloxy group are preferred.

An alkylthio group represents an alkylthio group which has a linear- or branched-chain or cyclic alkyl group having 1 to 12 carbon atoms. For example, it includes a methylthio group, an ethylthio group, n-propylthio group, an isopropylthio group, n-butylthio group, an isobutylthio group, sec-butylthio group, tert-butylthio group, a cyclopropylthio group, a cyclobutylthio group, a cyclopentylthio group and a cyclobutylthio group.

An alkylsulfonyl group represents an alkylsulfonyl group which has a linear- or branched-chain or cyclic alkyl group having 1 to 12 carbon atoms. For example, it includes a methanesulfonyl group, an ethanesulfonyl group, a propanesulfonyl group, a butanesulfonyl group, a pentanesulfonyl group, a hexanesulfonyl group, a heptanesulfonyl group, an octanesulfonyl group, a nonanesulfonyl group, a decanesulfonyl group, an undecanesulfonyl group and a dodecanesulfonyl group.

An acyl group represents a formyl group, an acyl group which has a linear- or branched-chain or cyclic alkyl group having 1 to 6 carbon atoms, an acyl group which has a linear- or branched-chain or cyclic alkenyl group having 1 to 6 carbon atoms, an acyl group which has a linear- or branched-chain or cyclic alkynyl group having 1 to 6 carbon atoms, or an acyl group which has an aryl group that may be substituted. Examples thereof are a formyl group, an acetyl group, a propionyl group, a butyryl group, an isobutyryl group, a valeryl group, an isovaleryl group, a pivaloyl group, a hexanoyl group, an acryloyl group, a metacryloyl group, a crotonoyl group, an isocrotonoyl group, a benzoyl group and a naphthoyl group.

An acyloxy group represents a formyloxy group, an acyloxy group which has a linear- or branched-chain or cyclic alkyl group having 1 to 6 carbon atoms, or an acyloxy group which has an aryl group that may be substituted. For example, it includes a formyloxy group, an acetyloxy group, a propionyloxy group, a butyryloxy group, an isobutyryloxy group, a valeryloxy group, an isovaleryloxy group, a pivaloyloxy group, a hexanoyloxy group, an acryloyloxy group, a metacryloyloxy group, a crotonoyloxy group, an isocrotonoyloxy group, a benzoyloxy group and a naphthoyloxy group.

An alkylamino group represents an amino group which is monosubstituted or disubstituted with an alkyl group(s), and examples of the alkyl group(s) are the same as those mentioned in the above "alkyl group." Concretely, they include an amino group, a methylamino group, an ethylamino group, a propylamino group, isopropylamino group, a dimethylamino group, a diethylamino group, a dipropylamino group, a diisopropylamino group and a methylethylamino group.

An alkoxycarbonyl group represents an alkoxycarbonyl group which has a linear- or branched-chain or cyclic alkyl group having 1 to 8 carbon atoms. Examples thereof are a methoxycarbonyl group, an ethoxycarbonyl group, a propoxycarbonyl group, an isopropoxycarbonyl group, n-butoxycarbonyl group, an isobutoxycarbonyl group, sec-butoxycarbonyl group, tert-butoxycarbonyl group and a benzyloxycarbonyl group.

A carbamoyl group represents a carbamoyl group which may have a linear- or branched-chain or cyclic alkyl group having 1 to 6 carbon atoms on a nitrogen. For example, it includes a carbamoyl group, N-methylcarbamoyl group, N-ethylcarbamoyl group, N,N-dimethylcarbamoyl group, N-pyrrolidylcarbonyl group, N-piperidylcarbonyl group and N-morpholinylcarbonyl group.

A sulfonyl group represents a sulfonyl group which may have a linear- or branched-chain or cyclic alkyl group having 1 to 6 carbon atoms on a sulfur atom. For example, it includes a methylsulfonyl group, an ethylsulfonyl group, a propylsulfonyl group and a butylsulfonyl group.

An aromatic ring represents a monocyclic or bicyclic aromatic ring which is composed of a carbon atom(s). For example, it includes a benzene ring, a naphthalene ring, an indene ring and a fluorene ring, and a benzene ring and a naphthalene ring are preferred.

A heterocyclic ring represents a heterocyclic ring consisting of one, two or three five- to seven-membered ring(s) composed of a carbon and a nitrogen, an oxygen, a sulfur and the like. For example, it includes a pyridine ring, a dihydropyran ring, a pyridazine ring, a pyrimidine ring, a pyrazine ring, a pyrrole ring, a furan ring, a thiophene ring, an oxazole ring, an isooxazole ring, a pyrazole ring, an imidazole ring, a thiazole ring, an isothiazole ring, a thiadiazole ring, a pyrrolidine ring, a piperidine ring, a piperazine ring, an indole ring, an isoindole ring, a benzofuran ring, an isobenzofuran ring, a benzothiophene ring, a benzopyrazole ring, a benzoimidazole ring, a benzooxazole ring, a benzothiazole ring, a purine ring, a pyrazolopyridine ring, a quinoline ring, an isoquinoline ring, a naphthyridine ring, a quinazoline ring, a benzodiazepine ring, a carbazole ring and a dibenzofuran ring. A pyridine ring, a pyrimidine ring and a thiophene ring are preferred among them.

An aliphatic ring represents a monocyclic or bicyclic aliphatic ring which is composed of a carbon atom(s). For example, it includes a cyclopropane ring, a cyclobutane ring, a cyclopenane ring, a cyclohexane ring, a cycloheptane ring, a cyclooctane ring, a decalin ring and a norbornane ring, and a cylohexane ring is preferred.

An heteroaryl group represents a heteroaromatic substituent consisting of one, two or three five- to seven-membered ring(s) composed of a carbon and a nitrogen, an oxygen, a sulfur and the like. For example, it includes a pyridyl group, a pyridazinyl group, a pyrimidinyl group, a pyrazinyl group, a pyrrolyl group, a furanyl group, a thienyl group, an oxazolyl group, an isooxazolyl group, a pyrazolyl group, an imidazolyl group, a thiazolyl group, an isothiazolyl group, a thiadiazolyl group, an indolyl group, an isoindolyl group, a benzofuryl group, an isobenzofuryl group, a benzothienyl group, a benzopyrazolyl group, a benzoimidazolyl group, a benzooxazolyl group, a benzothiazolyl group, a quinolyl group, an isoquinolyl group, a naphthyridinyl group and a quinazolyl group. A 2-pyridyl group, 3-pyridyl group, 4-pyridyl group and a 1-pyrazolyl group are preferred among them.

An aryloxy group is an aryloxy group having an aryl group(s) on an oxygen atom, and examples of the aryl group(s) are the same as those mentioned in the above "aryl group." Concretely, they include a phenoxy group, a 1-naphthyloxy group and 2-naphthyloxy group.

A heteroaryloxy group is an heteroaryloxy group having a heteroaryl group(s) on an oxygen atom, and examples of the heteroaryl group(s) are the same as those mentioned in the above "heteroaryl group." Concretely, they include a 2-pyridyloxy group, 3-pyridyloxy group, 4-pyridyloxy group and a 2-pyrimidinyl group.

An arylamino group is an arylamino group having an aryl group(s) on a nitrogen atom and examples of the aryl group(s) are the same as those mentioned in the above "aryl group." Concretely, they include a phenylamino group, 1-naphthylamino group and 2-naphthylamino group.

An arylvinyl group is a vinyl group of which the first position or the second position is substituted with an aryl group(s), and examples of the aryl group(s) are the same as those mentioned in the above "aryl group." Concretely, they include a 1-phenylvinyl group and 2-phenylvinyl group.

An arylethynyl group is an ethynyl group of which the second position is substituted with an aryl group(s), and examples of the aryl group(s) are the same as those mentioned in the above "aryl group." Concretely, they include a phenylethynyl group.

The term "which may have a substituent(s)" indicates the case in which a group does not have any substituents and the case in which, if a group has a substituent(s), one or more thereof are substituted with the substituent(s) mentioned in the above (I). The substituent(s) may be same or different from each other, and the position and number thereof are optional and not particularly limited.

Further, in the present invention, the compound of the formula (I) or pharmaceutically acceptable salts thereof are preferably those mentioned below.

$R^1$ is preferably a hydrogen atom and a methyl group.

$R^2$, $R^3$ and $R^4$ are preferably a hydrogen atom, a halogen atom, a hydroxy group, an alkyl group, an alkoxy group, an alkylthio group, an acyl group, an acyloxy group, an amino group, an alkoxycarbonyl group, a carbamoyl group, a nitro group, a cyano group, a trifluoromethyl group, an aryl group which may have a substituent(s), a heteroaryl group which may have a substituent(s), a benzyloxy group, an aryloxy group which may have a substituent(s) or an arylethynyl group which may have a substituent(s). More preferred ones are a hydrogen atom, a halogen atom, a hydroxy group, a methyl group, an ethyl group, a propyl group, an isopropyl group, a cyclopropyl group, a methoxy group, an ethoxy group, n-propoxy group, an isopropoxy group, a cyclopropoxy group, n-butoxy group, a benzyloxy group, a methylthio group, an ethylthio group, a trifluoromethoxy group and a trifluoromethyl group.

—X— is preferably —NH—, —NR$^5$— wherein R$^5$ represents a lower alkyl group, —S— or —CH$_2$—. Among them, —NH— or —NMe— is more preferred.

—Y— is preferably —NH—, —NR$^5$— wherein R$^5$ represents an acyl group which may have a substituent(s), an alkoxycarbonyl group which may have a substituent(s), a carbamoyl group which may have a substituent(s) or a sulfonyl group which may have a substituent(s), or —O—. Among them, —NR$^5$— wherein R$^5$ represents an acyl group which may have a substituent(s), an alkoxycarbonyl group which may have a substituent(s) or a carbamoyl group which may have a substituent(s) is more preferred, and —NAc—, —N(COCH$_2$CH$_3$)—, —N(COCH$_2$CF$_3$)—, —N(COCF$_2$CF$_3$)—, —N(COCH$_2$OEt)—, —N(COCH$_2$OH)—, —N(COOMe)— or —N(COOEt)— is further preferred.

-Z- is preferably —NH— or —CH$_2$—, and —CH$_2$— is more preferable.

—W— is preferably —NH—, —NR$^1$— wherein R$^1$ represents a lower alkyl group, or —CH$_2$—, and —NH— or —NMe— is more preferred.

Further, it is preferable that, in the formula (I), —X— and —Y— may be same or different from each other and represent —NH— or —NR$^5$— wherein R$^5$ represents a lower alkyl group which may have a substituent(s), an acyl group which may have a substituent(s), an alkoxycarbonyl group which may have a substituent(s), a carbamoyl group which may have a substituent(s) or a sulfonyl group which may have a substituent(s), and -Z- represents —CH$_2$— or —CR$^6$R$^7$— wherein R$^6$ and R$^7$ may be same or different from each other and each independently represents a hydrogen atom, a halogen atom, a hydroxy group, an alkyl group, a mercapto group, an alkoxy group, an alkylthio group, an alkylsulfonyl group, an acyl group, an acyloxy group, an amino group, an alkylamino group, a carboxyl group, an alkoxycarbonyl group, a carbamoyl group, a nitro group, a cyano group or a trifluoromethyl group; and further preferably —W— represents —NR$^1$— wherein R$^1$ represents a hydrogen atom, a lower alkyl group which may have a substituent(s) or an aryl group which may have a substituent(s). Here, a substituent(s) which may be had in R$^5$ is particularly preferably a hydroxy group, a mercapto group, an alkoxy group and an alkylthio group.

Ring A is preferably an aromatic ring or a heterocyclic ring. A benzene ring, a pyridine ring, a pyrimidine ring and a thiophene ring are more preferred among them, and a benzene ring is further more preferred.

Ring B is preferably an aromatic ring which may have a substituent(s) or an aliphatic ring which may have a substituent(s). A benzene ring which may have a substituent(s) or a cyclohexane ring which may have a substituent(s) is more preferred among them, and a cyclohexane ring which may have a substituent(s) is further more preferred.

When Ring B is a cyclohexane ring which may have a substituent(s), the absolute position of a carbon atom in a and b is preferably R or S, and R is further more preferred.

The compounds of the formula (I) are, for example, preferably those of Table 1 and Table 2. In addition to them, the compound described in WO02/44180 is also a preferable example. They are the compounds having a high sugar transportation activity by themselves as mentioned in following Table 3, and therefore, useful as agents for preventing and/or treating diabetes, diabetic complication, hyperinsulinemia, glucose intolerance or obesity.

In the compound of the formula (I) used in the present invention, it is particularly preferable that —X— represents —NH—, —Y— represents —NAc—, —N(COCH$_2$CH$_3$)—, —N(COCH$_2$CF$_3$)—, —N(COCH$_2$OEt)— or —N(COCH$_2$OH)—, -Z- represents —CH$_2$—, —W— represents —NH—, Ring A represents a benzene ring, and Ring B represents a cyclohexane ring which may have a substituent(s). Further, in Table 1 and 2, the Compound Nos. 6, 8, 62, 80, 81, 88, 91, 96, 98, 105, 106, 129, 130, 131 and 132 are particularly preferable.

TABLE 1

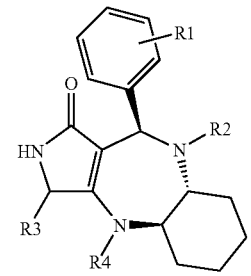

| No | R1 | R2 | R3 | R4 |
|----|------|------------------------------|----|----|
| 1  | 2-OMe | COCH$_3$ | H | H |
| 2  | 2-OMe | COCH$_2$CH$_3$ | H | H |
| 3  | 2-OMe | COCH$_2$CH$_2$CH$_3$ | H | H |
| 4  | 2-OMe | CO—cyclopropyl | H | H |
| 5  | 2-OMe | COCF$_3$ | H | H |
| 6  | 2-OMe | COCH$_2$CF$_3$ | H | H |
| 7  | 2-OMe | COCF$_2$CF$_3$ | H | H |
| 8  | 2-OMe | COCH$_2$OH | H | H |
| 9  | 2-OMe | COCH$_2$OAc | H | H |
| 10 | 2-OMe | COCH$_2$OMe | H | H |
| 11 | 2-OMe | COCH$_2$OEt | H | H |
| 12 | 2-OMe | COCH$_2$OPh | H | H |
| 13 | 2-OMe | COCH$_2$Ph | H | H |
| 14 | 2-OMe | COCH=CHPh | H | H |
| 15 | 2-OMe | COC≡CPh | H | H |
| 16 | 2-OMe | COCH=CHCH$_3$ | H | H |
| 17 | 2-OMe | COCH$_2$CH$_2$COOMe | H | H |
| 18 | 2-OMe | COCH$_2$CH$_2$COOH | H | H |
| 19 | 2-OMe | COCH$_2$CH$_2$CH$_2$OH | H | H |
| 20 | 2-OMe | COCH$_2$NHZ | H | H |
| 21 | 2-OMe | COCH$_2$NH$_2$ | H | H |
| 22 | 2-OMe | COCH$_2$CH$_2$NHZ | H | H |
| 23 | 2-OMe | COCH$_2$CH$_2$NH$_2$ | H | H |
| 24 | 2-OMe | COCH$_2$CH$_2$OMe | H | H |
| 25 | 2-OMe | COCH$_2$CH$_2$Ph | H | H |
| 26 | 2-OMe | COCH$_2$—(2-OMe—Ph) | H | H |
| 27 | 2-OMe | COCH$_2$CH$_2$—(3,4-F$_2$—Ph) | H | H |
| 28 | 2-OMe | COCH$_2$CH$_2$SMe | H | H |
| 29 | 2-OMe | COCH$_2$COCH$_3$ | H | H |
| 30 | 2-OMe | COCH$_2$COOEt | H | H |
| 31 | 2-OMe | COCOOEt | H | H |

TABLE 1-continued

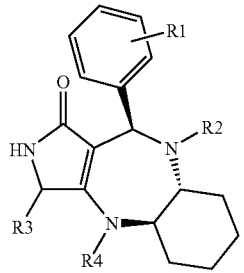

| No | R1 | R2 | R3 | R4 |
|---|---|---|---|---|
| 32 | 2-OMe | COPh | H | H |
| 33 | 2-OMe | CO—2-pyridyl | H | H |
| 34 | 2-OMe | CO—3-pyridyl | H | H |
| 35 | 2-OMe | CO—4-pyridyl | H | H |
| 36 | 2-OMe | CO—2-pyrazyl | H | H |
| 37 | 2-OMe | COOMe | H | H |
| 38 | 2-OMe | COOEt | H | H |
| 39 | 2-OMe | COOCH$_2$Ph | H | H |
| 40 | 2-OMe | COOPh | H | H |
| 41 | 2-OMe | CONHEt | H | H |
| 42 | 2-OMe | CONHCH$_2$CH$_2$CH$_3$ | H | H |
| 43 | 2-OMe | SO$_2$CH$_3$ | H | H |
| 44 | 2-OMe | COCH$_3$ | Me | Me |
| 45 | 2-OMe | CH$_3$ | H | H |
| 46 | 2-OEt | COCH$_3$ | H | H |
| 47 | 2-OEt | COCH$_2$CH$_3$ | H | H |
| 48 | 2-OEt | COCH$_2$CH$_2$CH$_3$ | H | H |
| 49 | 2-OEt | COCF$_3$ | H | H |
| 50 | 2-OEt | COCH$_2$OAc | H | H |
| 51 | 2-OEt | COCH$_2$OH | H | H |
| 52 | 2-OEt | COCH$_2$OMe | H | H |
| 53 | 2-OEt | COCH$_2$OEt | H | H |
| 54 | 2-OEt | COOMe | H | H |
| 55 | 2-OEt | COOEt | H | H |
| 56 | 2-OEt | CONHEt | H | H |
| 57 | 2-OCHMe$_2$ | COCH$_3$ | H | H |
| 58 | 2-OCHMe$_2$ | COCH$_2$CH$_3$ | H | H |
| 59 | 2-OCHMe$_2$ | COCH$_2$OEt | H | H |
| 60 | 2-OCHMe$_2$ | COOMe | H | H |
| 61 | 2-cyclopropoxy | COCH$_3$ | H | H |
| 62 | 2-cyclopropoxy | COCH$_2$OH | H | H |
| 63 | 2-OCH$_2$Ph | COCH$_2$OEt | H | H |
| 64 | 2-OCH$_2$Ph | COCH$_3$ | H | H |
| 65 | 2-OH | COCH$_2$OEt | H | H |
| 66 | 2-OH | COCH$_3$ | H | H |
| 67 | 2-OCF$_3$ | COCH$_3$ | H | H |
| 68 | 2-OCF3 | COCH2OH | H | H |
| 69 | 2-OCF3 | COCH$_2$OMe | H | H |
| 70 | 2-OMe—4-F | COCH$_2$CH$_3$ | H | H |
| 71 | 2-OMe—4-F | COCH$_2$OEt | H | H |
| 72 | 2-OMe—4-F | COCH$_3$ | H | H |
| 73 | 2-OMe—4-Cl | COCH$_3$ | H | H |
| 74 | 2-OMe—4-OCH$_2$Ph | COCH$_3$ | H | H |
| 75 | 2-OMe—4-OH | COCH$_3$ | H | H |
| 76 | 2-OMe—5-F | COCH$_3$ | H | H |
| 77 | 2,3-(OMe)$_2$ | COCH$_3$ | H | H |
| 78 | 2,4-(OMe)$_2$ | COCH$_3$ | H | H |
| 79 | 2,5-(OMe)$_2$ | COCH$_3$ | H | H |
| 80 | 2-SMe | COCH$_3$ | H | H |
| 81 | 2-SMe | COCH$_2$OH | H | H |
| 82 | 2-Me | COCF$_3$ | H | H |
| 83 | 2-Me | COCH$_2$CH$_3$ | H | H |
| 84 | 2-Me | COCH$_2$OEt | H | H |
| 85 | 2-Me | COCH$_2$OAc | H | H |
| 86 | 2-Me | COCH$_2$OH | H | H |
| 87 | 2-Me | COCH$_2$OMe | H | H |
| 88 | 2-Me | COCH$_3$ | H | H |
| 89 | 2-Me | COOEt | H | H |
| 90 | 2-Me | COOMe | H | H |
| 91 | 2-Me | COCH$_2$CH$_3$ | H | Me |
| 92 | 2-Me | COCH2OH | H | Me |
| 93 | 2-Et | COCH$_2$CH$_2$CH$_3$ | H | H |
| 94 | 2-Et | COCH$_2$CH$_3$ | H | H |
| 95 | 2-Et | COCH$_2$COOMe | H | H |
| 96 | 2-Et | COCH$_2$OEt | H | H |
| 97 | 2-Et | COCH$_2$OMe | H | H |
| 98 | 2-Et | COCH$_3$ | H | H |
| 99 | 2-Et | COOMe | H | H |
| 100 | 2-Et | COCH$_3$ | (S)-Me | H |
| 101 | 2-Et | COCH$_2$CH$_3$ | (S)-Me | H |
| 102 | 2-Et | COCH$_3$ | H | Et |
| 103 | 2-CHMe$_2$ | COCH$_3$ | H | H |
| 104 | 2-cyclopropyl | COCH$_2$OH | H | H |
| 105 | 2-cyclopropyl | COCH$_3$ | H | H |
| 106 | 2-Me, 3-F | COCH$_2$CH$_3$ | H | H |
| 107 | 2-Me, 3-F | COCH$_3$ | H | H |
| 108 | 2-Me—3-Cl | COCH$_2$OEt | H | H |
| 109 | 2-Br | COCH$_2$CF$_3$ | H | H |
| 110 | 2-Br | COCH$_2$CH$_3$ | H | H |
| 111 | 2-Br | COCH$_2$COOMe | H | H |
| 112 | 2-Br | COCH$_2$OEt | H | H |
| 113 | 2-Br | COCH$_2$OMe | H | H |
| 114 | 2-Br | COCH$_3$ | H | H |
| 115 | 2-Cl | COCH$_3$ | H | H |
| 116 | 2-Cl | COCH$_2$CH$_3$ | H | H |
| 117 | 2-Cl | COCH$_2$CH$_2$CH$_3$ | H | H |
| 118 | 2-Cl | COCH$_2$CF$_3$ | H | H |
| 119 | 2-Cl | COCH$_2$OMe | H | H |
| 120 | 2-Cl | COCH$_2$OEt | H | H |
| 121 | 2-Cl | COCH$_2$COOMe | H | H |
| 122 | 2-Cl | COOMe | H | H |
| 123 | 2-F | COCH$_3$ | H | H |
| 124 | 2-F | COCH$_2$CH$_3$ | H | H |
| 125 | 2-F | CO—cyclopropyl | H | H |
| 126 | 2-F | COCH$_2$OEt | H | H |
| 127 | 2-F | COOMe | H | H |
| 128 | 2-CF$_3$ | COCH$_3$ | H | H |
| 129 | H | COCH$_3$ | H | H |
| 130 | H | COCH$_2$CH$_3$ | H | H |
| 131 | H | COCH$_2$OH | H | H |
| 132 | H | COCH$_2$OEt | H | H |
| 133 | H | COOMe | H | H |
| 134 | H | CH$_2$COOEt | H | H |
| 135 | 2-NO$_2$ | COCH$_3$ | H | H |
| 136 | 2-NH$_2$ | COCH$_3$ | H | H |
| 137 | 3-Cl | COCH$_3$ | H | H |
| 138 | 4-OMe | COCH$_3$ | H | H |
| 139 | 4-Br | COCH$_3$ | H | H |
| 140 | 4-Cl | COCH$_3$ | H | H |
| 141 | 4-Cl | COCH$_2$OEt | H | H |

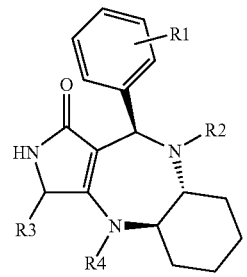

TABLE 2

| No | Structure |
|---|---|
| 142 | 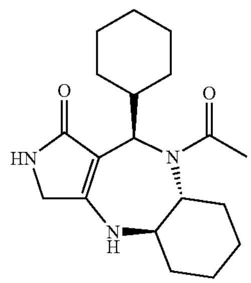 |
| 143 | 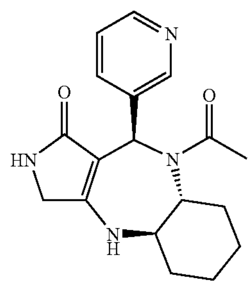 |
| 144 | 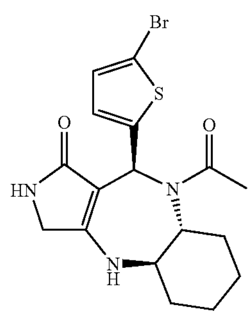 |
| 145 | 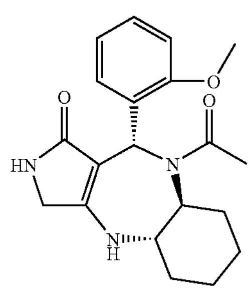 |
| 146 | 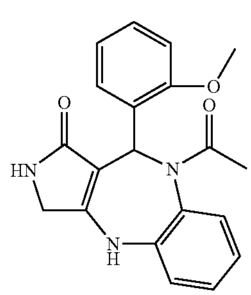 |

TABLE 2-continued

| No | Structure |
|---|---|
| 147 | 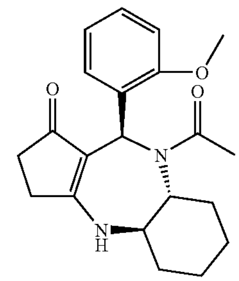 |
| 148 | 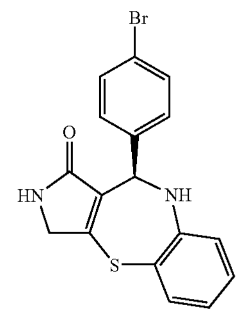 |
| 149 | 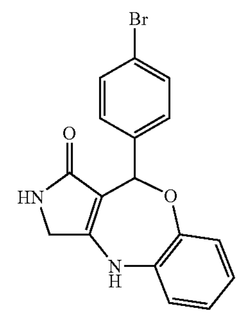 |
| 150 | 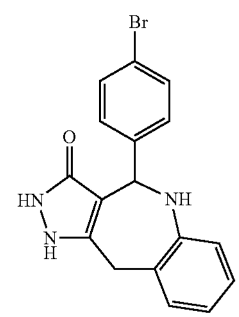 |

The pharmaceutically acceptable salts of the compound of the formula (I) include, for example, in the case of the compounds which are sufficiently acidic, ammonium salts thereof, alkali metal salts (such as sodium salts and potassium salts, as preferable examples), alkaline earth metal salts (such as calcium salts and magnesium salts, as preferable examples); as salts of an organic base, for example, dicyclohexylamine salts, benzathine salts, N-methyl-D-glucan salts, hydramine salts, and salts of an amino acids such as arginine and lysine. Further, in the case of the compounds which are sufficiently basic, the salts include acid addition salts thereof, such as those with inorganic acids, e.g. hydrochloric acid, sulfuric acid, nitric acid and phosphoric acid; or those with organic acids, e.g. acetic acid, lactic acid, citric acid, tartaric acid, maleic acid, fumaric acid and monomethyl sulfate. In some cases, they may be wet salts or hydrates.

The compound of the formula (I) includes all isomers such as optical isomers and geometric isomers, hydrates, solvates or crystal forms.

Meanwhile, the compound of the formula (I) can be synthesized by the producing method described in WO02/44180, for instance. The compound of the present invention obtained by synthesis can be purified with ordinary methods such as extraction, distillation, crystallization and column chromatography.

In the present invention, examples of drug products which can be used by combining with the compound of the formula (I) include one of insulin preparations, insulin derivatives, insulin-like agonists, insulin secretagogues, insulin sensitizers, biguanides, gluconeogenesis inhibitors, sugar absorption inhibitors, renal glucose re-uptake inhibitors, β3 adrenergic receptor agonists, glucagon-like peptide-1, analogues of glucagon-like peptide-1, glucagon-like peptide-1 receptor agonists, dipeptidyl peptidase IV inhibitors, aldose reductase inhibitors, advanced glycation endproducts production inhibitors, glycogen synthase kinase-3 inhibitors, glycogen phosphorylase inhibitors, antilipemic agents, anorexic agents, lipase inhibitors, antihypertensive agents, peripheral circulation improving agents, antioxidants and diabetic neuropathy therapeutic agents, a combination of two or more of these agents or mixture thereof.

When the compound of the formula (I) and one or more kind(s) of the above agent(s) are combined to use, the present invention includes all administration forms of simultaneous administration as a single drug product thereof, simultaneous administration through the same or different route as separate drug products thereof, and administration having intervals through the same or different route as separate drug products thereof. The pharmaceutical compositions comprising the step of combining the compound of the formula (I) with the above agent(s) include the administration form as a single drug product thereof and also the administration form by combining separate drug products thereof as mentioned above.

By use of the combination of the compound of the formula (I) and one or more kind(s) of the above agent(s) accordingly, favorable effect more than a mere additive effect can be obtained for preventing or treating the above diseases. Similarly, compared with a single use, usage of the compound of the formula (I) can be decreased, or side effects of at least one kind of the agent(s) selected from above Group A used together can be prevented or alleviated.

The specific compounds of the agents used by combination and diseases which should be treated suitably are illustrated as follows, which by no means limit the present invention. In the specific compounds, free forms thereof and/or other pharmaceutically acceptable salts are included.

Examples of the Insulin preparations include human insulin and insulin of animal origin. For example, they include NPH, lente, ultralente and transpulmonary sorbable insulin.

Insulin analogues represent insulin-induced proteins or peptides, which retain insulin action. Examples thereof are lyspro, aspart and glargine.

Insulin-like agonists represent those but insulin analogues, which achieve hypoglycemic action by producing physiologic activities of insulin such as the action promoting sugar-uptake into cells without depending on insulin to some extent. They include, for example, insulin receptor kinase stimulants (such as L-783281, TER-17411, CLX-0901 and KRX-613) and vanadium.

Insulin secretagogues represent those which achieve hypoglycemic action by affecting pancreatic β cells and reinforcing secretion of insulin into blood. For example, they include sulfonylurea agents (such as tolbutamide, chlorpropamide, tolazamide, acetohexamide, gliclazide, glimepiride, glipizide and glibenclamide (glyburide)), meglitinides (such as nateglinide, repaglinide and mitiglinide), and ATP sensitive potassium channel inhibitors (such as BTS-67-582) other than sulfonylurea agents/meglitinides.

Insulin sensitizers represent those which achieve hypoglycemic action by reinforcing insulin action in target tissues of insulin. For instance, they include peroxisome proliferator-activated receptor (PPAR)γ agonists (for example, thiazolidinedione compounds e.g. glitazones such as pioglitazone, rosiglitazone, troglitazone and ciglitazone; or non-thiazolidinedione compounds e.g. GI-262570, GW-1929, JTT-501 and YM-440), PPARγ antagonists (such as bisphenol A diglycidyl ether and LG-100641), PPARα agonists (for example, fibrate compounds such as clofibrate, bezafibrate and clinofibrate; or non-fibrate compounds), PPARα/γ agonists (such as KRP-297), retinoid X receptor agonists (such as LG-100268), retinoid X receptor antagonists (such as HX531) and protein tyrosine phosphatase 1B inhibitors (such as PTP-112).

Biguanides represent those which achieve hypoglycemic action by gluconeogenesis inhibiting action in a liver, anaerobic glycolysis promoting action in tissues or insulin resistance improving action in peripheries. They include, for example, metformin, phenformin and buformin.

Gluconeogenesis inhibitors represent those which achieve hypoglycemic action by inhibiting gluconeogenesis mainly, and include glucagon secretion inhibitors (such as M & B 39890A), glucagon receptor antagonists (such as CP-99711, NNC-92-1687, L-168049 and BAY27-9955), glucose-6-phosphatase inhibitors and the like.

Sugar absorption inhibitors represent those which achieve hypoglycemic action by inhibiting enzymatic digestion of carbohydrates in food in digestive tracts, and inhibiting or slowing sugar uptake in the body. For example, they include α-glucosidase inhibitors (such as acarbose, voglibose and miglitol) and α-amylase inhibitors (such as AZM-127).

Renal glucose re-uptake inhibitors represent those which achieve hypoglycemic action by inhibiting re-uptake of sugar in renal tubules, and include, for example, sodium-dependent glucose transporter inhibitors (such as T-1095 and phlorizin).

β3 adrenergic receptor agonists represent those which achieve improving action of obesity and hyperinsulinemia by stimulating β3 adrenergic receptor in fats and fatty-acid oxidation to consume energy. For example, they include CL-316243 and TAK-677.

Analogues of glucagon-like peptide-1 include, for instance, exendin-4 and NN-2211; glucagon-like peptide-1 receptor agonists include AZM-134 and the like; and dipeptidyl peptidase IV inhibitors include NVP-DPP-728, for example. Analogues of glucagon-like peptide-1, glucagon-like peptide-1 receptor agonists, dipeptidyl peptidase IV inhibitors and glucagon-like peptide-1 represent those which achieve the action of improving diabetes by mimicking or reinforcing the action of glucagon-like peptide-1 in cells.

Aldose reductase inhibitors, among those suitable for the treatment of diabetic complication, represent those which decrease intracellular sorbitols by inhibiting aldose reductases, and said sorbitols accumulate excessively by enhancement of a course of polyol metabolism which is induced by continuous hyperglycemia shown in tissues developing diabetic complication. They include, for example, epalrestat, tolrestat, fidarestat and zenerestat.

Advanced glycation endproducts production inhibitors, among those suitable for the treatment of diabetic complication, represent those which alleviate cell disorders by inhibiting production of advanced glycation endproducts which are increased by continuous hyperglycemia in a diabetic state. NNC-39-0028 and OPB-9195 are examples thereof.

Glycogen synthase kinase-3 inhibitors include, for example, SB-216763 and CHIR-98014; and glycogen phosphorylase inhibitors include CP-91149 and the like.

Antilipemic agents include hydroxymethylglutaryl-CoA reductase inhibitors (such as pravastatin, simvastatin, fluvastatin and atorvastatin), fibrate agents (such as clofibrate, bezafibrate and simfibrate) and cholaneresis drugs.

Anorexic agents include, for example, sibutramine and mazindol; and lipase inhibitors include orlistat.

Examples of antihypertensive agents are inhibitors of angiotensin converting enzyme (such as captopril and alacepril), angiotensin II receptor antagonists (such as candesartan cilexetil and valsartan), calcium antagonists (such as cilnidipine, amlodipine and nicardipine), diuretic agents (such as trichlormethiazide and spironolactone) and sympatholytic agents (such as clonidine and reserpine).

Peripheral circulation improving agents include, for example, ethyl icosapentate.

Antioxidants include a lipoic acid and probucol.

Examples of diabetic neuropathy therapeutic agents are mecobalamin and mexiletine hydrochloride.

Further, unexplained hypoglycemic agents, antilipemic agents, anti-obesity agents, antihypertensive agents, peripheral circulation improving agents, antioxidants and diabetic neuropathy therapeutic agents are also included in the present invention, as long as they are combined with the compound of the formula (I) to use.

Among the drug products of above Group A, insulin preparations, insulin secretagogues, insulin sensitizers, biguanides and sugar absorption inhibitors are preferred. Here, more preferred ones are NPH as the insulin preparations, sulfonylurea agents and meglitinides as the insulin secretagogues, peroxisome proliferator-activated receptor (PPAR)$_\gamma$ agonists (particularly thiazolidinedione compounds such as pioglitazone, rosiglitazone, troglitazone and ciglitazone) as insulin sensitizers, and α-glucosidase inhibitors (particularly acarbose and voglibose) as sugar absorption inhibitors. Among them, insulin secretagogues and biguanides are particularly preferable in the present invention, and sulfonylurea agents such as gliclazide, glimepiride and glibenclamide; meglitinides such as nateglinide, repaglinide and mitiglinide; and biguanides such as metformin, phenformin and buformin are further more preferable.

Diseases caused by hyperglycemia include diabetes, diabetic complication (for example, retinopathy, neuropathy, nephropathy, ulcers, macroangiopathy), obesity, hyperinsulinemia, disorders of sugar metabolism, hyperlipemia, hypercholesteremia, hypertriglyceridemia, disorders of lipid metabolism, atherosclerotic cardiovascular disease, hypertension, congestive failure, edema, hyperuricemia and gout.

For example, when the compound of the formula (I) and at least one kind of an agent selected from above Group A are combined to use, it is preferable in the treatment of diabetes to combine said compound with at least one kind of an agent selected from the group consisting of insulin preparations, insulin derivatives, insulin-like agonists, insulin secretagogues, insulin sensitizers, biguanides, gluconeogenesis inhibitors, sugar absorption inhibitors, renal glucose re-uptake inhibitors, β3 adrenergic receptor agonists, glucagon-like peptide-1, analogues of glucagon-like peptide-1, glucagon-like peptide-1 receptor agonists, dipeptidyl peptidase IV inhibitors, glycogen synthase kinase-3 inhibitors, glycogen phosphorylase inhibitors, anorexic agents and lipase inhibitors. It is further preferable to combine it with at least one kind of an agent selected from the group consisting of insulin preparations, insulin derivatives, insulin-like agonists, insulin secretagogues, insulin sensitizers, biguanides, gluconeogenesis inhibitors, sugar absorption inhibitors, renal glucose re-uptake inhibitors, β3 adrenergic receptor agonists, glucagon-like peptide-1, analogues of glucagon-like peptide-1, glucagon-like peptide-1 receptor agonists, dipeptidyl peptidase IV inhibitors, glycogen synthase kinase-3 inhibitors and glycogen phosphorylase inhibitors; and it is most preferable to combine it with at least one kind of an agent selected from the group consisting of insulin preparations, insulin derivatives, insulin-like agonists, insulin secretagogues, insulin sensitizers, biguanides, gluconeogenesis inhibitors, sugar absorption inhibitors and renal glucose re-uptake inhibitors. Among these, particularly preferred ones are insulin; gliclazide, glimepiride and glibenclamide which are sulfonylurea agents; nateglinide, repaglinide and mitiglinide which are meglitinides; pioglitazone and rosiglitazone which are glitazones; metformin, phenformin and buformin which are biguanides; and acarbose, voglibose and miglitol which are α-glucosidase inhibitors.

Similarly, when the compound of the formula (I) and at least one kind of an agent selected from above Group A are combined to use, it is preferable in the treatment of diabetic complication to combine said compound with at least one kind of an agent selected from the group consisting of insulin preparations, insulin derivatives, insulin-like agonists, insulin secretagogues, insulin sensitizers, biguanides, gluconeogenesis inhibitors, sugar absorption inhibitors, renal glucose re-uptake inhibitors, β3 adrenergic receptor agonists, glucagon-like peptide-1, analogues of glucagon-like peptide-1, glucagon-like peptide-1 receptor agonists, dipeptidyl peptidase IV inhibitors, aldose reductase inhibitors, advanced glycation endproducts production inhibitors, glycogen synthase kinase-3 inhibitors, glycogen phosphorylase inhibitors, antilipemic agents, anorexic agents, lipase inhibitors, antihypertensive agents, peripheral circulation improving agents, antioxidants and diabetic neuropathy therapeutic agents. It is further preferable to combine it with at least one kind of an agent selected from the group consisting of aldose reductase inhibitors, advanced glycation endproducts production inhibitors, antihypertensive agents, peripheral circulation improving agents, antioxidants and diabetic neuropathy therapeutic agents.

Further, it is preferable in the treatment of obesity to combine said compound with at least one kind of an agent selected from the group consisting of insulin preparations, insulin derivatives, insulin-like agonists, insulin secretagogues, insulin sensitizers, biguanides, gluconeogenesis inhibitors, sugar absorption inhibitors, renal glucose re-uptake inhibitors, β3 adrenergic receptor agonists, glucagon-like peptide-1, analogues of glucagon-like peptide-1, glucagon-like peptide-1 receptor agonists, dipeptidyl peptidase IV inhibitors, glycogen synthase kinase-3 inhibitors, glycogen phosphorylase inhibitors, anorexic agents and lipase inhibitors. It is further more preferable to combine it with at least one kind of an agent selected from the group consisting of β3 adrenergic receptor agonists, anorexic agents and lipase inhibitors.

In the pharmaceutical compositions combining the compound of the formula (I) of the present invention with at least one kind of an agent selected from above Group A, combination way thereof may be a single drug product by putting both together, a single package as a kit with separate drug products, or separate packages. The ratio of the compound of the formula (I) and at least one kind of an agent selected from above Group A depends on many factors such as intended dose and a used pharmaceutically acceptable carrier(s), and, therefore, can differ extensively. However, in both cases of a single drug product by putting both together and separate drug products, it is preferable that at least one kind of an agent selected from above Group A (however, insulin preparations, insulin derivatives, glucagon-like peptide-1 or analogues of glucagon-like peptide-1) is about 0.01 to 100 to content (weight) 1 of the compound of the formula (I). When agents combined with the compound of the formula (I) are insulin preparations, insulin derivatives, glucagon-like peptide-1 and analogues of glucagon-like peptide-1, they are 0.1 to 500 U to content (weight) 1 of the compound of the formula (I). The pharmaceutical compositions of the present invention are for diseases induced by hyperglycemia, diabetes, diabetic complication, hyperinsulinemia, glucose intolerance or obesity, and can be used for preventing and/or treating them.

When the present pharmaceutical compositions are applied to patients as a single drug product, each they can be administered so that each component is within the above range. When each active ingredient is administered as a separate drug product, the above ratio can be applied to as an average ratio.

Per one drug product for the present invention, it is preferable that about 0.01 to 1000 mg of the compound of the formula (I), and about 0.01 to 2000 mg of an agent selected from above Group A (however, 0.1 to 500 U in case of insulin preparations, insulin derivatives, glucagon-like peptide-1 or analogues of glucagon-like peptide-1) can be included.

When the pharmaceutical compositions of the present invention are used, they can be administered orally, intravenously, subcutaneously or intramuscularly. The dosage differs depending on a patient's symptom, age and administration method. It is preferable that the compound of the formula (I) is usually 0.001 to 1000 mg/kg/day and more preferably 1 to 3000 mg/man/day, and an agent selected from above Group A is 0.001 to 2000 mg however, 0.01 to 1000 U in case of insulin preparations, insulin derivatives, glucagon-like peptide-1 or analogues of glucagon-like peptide-1).

The pharmaceutical compositions of the present invention can be prepared by ordinary methods. The forms of drugs are, for example, injectable solvents, tablets, granules, subtle granules, powders, capsules, cream pharmaceuticals and suppositories. The preparation carriers include such as lactose, glucose, D-mannitol, starch, crystalline cellulose, calcium carbonate, kaolin, starch, gelatin, hydroxypropyl cellulose, hydroxypropyl methyl cellulose, polyvinylpyrrolidone, ethanol, carboxy methyl cellulose, carboxy methyl cellulose calcium salts, magnesium stearate, talc, acetyl cellulose, sucrose, titanium oxide, benzoic acid, p-hydroxybenzoate ester, sodium dehydroacetate, gum arabic, tragacanth, methyl cellulose, egg yolk, surfactants, sucrose, simple syrup, citric acid, distilled water, ethanol, glycerin, propylene glycols, macrogol, dibasic sodium phosphate, monobasic sodium phosphate, sodium phosphate, glucose, sodium chloride, phenol, thimerosal, p-hydroxybenzoate ester and acid sodium sulfite. They can be used by combining with the compound of the present invention depending on the forms of the drugs.

When the compound of the present invention is concretely administered, for example, the above amount of the Compound Nos. 6, 8, 62, 80, 81, 88, 91, 96, 98, 105, 106, 129, 130, 131 or 132 may be administered with the above applied amount of the either compounds of insulin, gliclazide, glimepiride, glibenclamide, nateglinide, repaglinide, mitiglinide, pioglitazone, rosiglitazone, metformin, phenformin, buformin, acarbose, voglibose or miglitol simultaneously or separately.

Next, Examples will further illustrate the present invention in detail. The following Examples only explain the present invention and do not particularly limit the invention.

Reference Example 1

Evaluation of the Sugar Transportation Activity

1. Preparation of Adipose Cells of Rats:

After the decapitation and venesection of 6 male Wistar rats (body weight: 150 to 200 g), an incision was made in the abdomen of each rat to extract 6 g in total of epididymal adipose tissues. The tissues were finely cut into 2 mm×2 mm pieces in 6 ml of KRH (Krebs-Ringer Hepes, composition: 130 mM of sodium chloride, 4.7 mM of potassium chloride, 1.2 mM of potassium dihydrogenphosphate, 1.2 mM of magnesium sulfate, 1 mM of calcium chloride and 25 mM of Hepes, pH=7.6) containing 5% of BSA (bovine serum albumin). 24 mg of collagenase (type I) was added thereto and the digestion treatment was conducted for about 40 minutes to obtain about 6 ml of isolated adipose cells. The collagenase was removed by the buffer exchange. 2% BSA/KRH solution was added to the residue for the re-suspension to obtain 45 ml of an adipose cell suspension.

2. Evaluation of the Sugar Transportation Activity:

The sugar transportation activity of the compound (I) of the present invention was evaluated with reference to a method described in a literature [Annual Review of Biochemistry, Vol. 55, p. 1059 (1986)]. In the test, 200 µL of the adipose cell suspension was poured in each polystyrene test tube, 100 µL of the solution of the test substance (by dilution of 10 mg/mL dimethyl sulfoxide solution with KRH) was added thereto, and the obtained mixture was shaken and then cultured at 37° C. for 30 minutes. The sugar transportation activity was evaluated by measuring the quantity of $2\text{-}[^{14}C(U)]\text{-deoxy-D-glucose}$ incorporated per a unit time. Namely, $2\text{-}[^{14}C(U)]\text{-deoxy-D-glucose}$ was added to the adipose cell suspension after the pre-culture (the final concentration: 0.5 µCi/sample). 5 minutes after, cytochalasin B (final concentration: 10 µM) was added to the mixture to terminate the sugar transportation. After forming a dinonyl phthalate layer, the obtained mixture was centrifuged to separate the adipose cells from the buffer. The quantity of $2\text{-}[^{14}C(U)]\text{-deoxy-D-glucose}$ contained in the adipose cell layer was determined with a liquid scintillation counter to determine the quantity of the incorporated sugar. In this evaluation system, when insulin (100 nM) having the effect of reinforcing the sugar transportation was used, the effect was about 7 times as high as that obtained in the insulin-free control group.

The results of the evaluation of the sugar transportation activity obtained by using 100 µg/mL of the compound (I) of the present invention are shown in Table 3. The sugar transportation activity in Table 3 was evaluated on the basis of the reinforcing effect of insulin (100 nM). The sugar transportation activity A in Table 3 was determined in terms of the concentration (EC50: µg/mL) of a test compound, having a reinforcing effect corresponding to 50% on the basis of the reinforcing effect of insulin (100 nM) having a reinforcing effect of 100%.

The symbols in Table 3 are as follows:
No: Compound No. in Tables 1 and 2, and
A: sugar transportation activity.

TABLE 3

| No | A |
| --- | --- |
| 1 | 1.3 |
| 2 | 0.77 |
| 3 | 4.6 |
| 4 | 0.5 |
| 5 | 4.5 |
| 6 | 0.47 |
| 7 | 9.5 |
| 8 | 2 |
| 9 | 5.9 |
| 10 | 2 |
| 11 | 2.2 |
| 12 | 4.6 |
| 13 | 5 |
| 16 | 1.1 |
| 17 | 4.8 |
| 19 | 4.8 |
| 22 | 8 |
| 23 | 8 |
| 24 | 3.4 |
| 25 | 0.9 |
| 26 | 4 |
| 27 | 4.2 |
| 28 | 2.6 |
| 29 | 5.5 |
| 33 | 10 |
| 34 | 20 |
| 35 | 18 |
| 36 | 8.6 |
| 37 | 6 |
| 38 | 4.2 |
| 39 | 6 |
| 40 | 11 |
| 41 | 3.6 |
| 42 | 7 |
| 46 | 15 |
| 47 | 1.9 |
| 48 | 1.3 |
| 49 | 5 |
| 50 | 13 |
| 51 | 3.8 |
| 52 | 3.6 |
| 53 | 4 |
| 54 | 1.5 |
| 55 | 7 |
| 56 | 12 |
| 57 | 14 |
| 58 | 2 |
| 59 | 2 |
| 60 | 4.8 |
| 61 | 0.9 |
| 62 | 0.5 |
| 63 | 4 |
| 64 | 3.6 |
| 65 | 1 |
| 66 | 3.7 |
| 67 | 20 |
| 68 | 2.7 |
| 69 | 2 |
| 70 | 0.82 |
| 71 | 7.8 |
| 72 | 8 |
| 73 | 6 |
| 75 | 20 |
| 76 | 10 |
| 77 | 12 |
| 78 | 10 |
| 80 | 5 |
| 81 | 2 |
| 82 | 6 |
| 83 | 2 |
| 84 | 4 |
| 85 | 8 |
| 86 | 2.5 |

TABLE 3-continued

| No | A |
| --- | --- |
| 87 | 6 |
| 88 | 5 |
| 89 | 7 |
| 90 | 2 |
| 91 | 0.45 |
| 92 | 1.5 |
| 93 | 5 |
| 94 | 2.2 |
| 95 | 2 |
| 96 | 5.4 |
| 97 | 6 |
| 98 | 4 |
| 99 | 4 |
| 100 | 10 |
| 101 | 7 |
| 102 | 5 |
| 103 | 20 |
| 104 | 0.8 |
| 105 | 0.5 |
| 106 | 0.6 |
| 107 | 6 |
| 108 | 5 |
| 109 | 0.5 |
| 110 | 1.5 |
| 111 | 1.5 |
| 112 | 8.6 |
| 113 | 6 |
| 114 | 6 |
| 115 | 20 |
| 116 | 3 |
| 117 | 4 |
| 118 | 0.5 |
| 119 | 5 |
| 120 | 10.7 |
| 121 | 2 |
| 122 | 2.4 |
| 123 | 20 |
| 124 | 2 |
| 125 | 2 |
| 126 | 2 |
| 127 | 2 |
| 129 | 20 |
| 130 | 1.5 |
| 131 | 1.5 |
| 132 | 2.7 |
| 133 | 2 |
| 135 | 20 |
| 136 | 12 |
| 138 | 4.4 |
| 139 | 17 |
| 141 | 6 |
| 144 | 19 |

Example 1

Investigation of a Combinational Effect with Insulin Secretagogues Using Normal Mise The compound (II) of the Compound No. 96 in above Table 1, which is indicated by the following structural formula, was used for the investigation. The compound is that described as Example 129 in WO02/44180 and synthesized in accordance with the method described in the international publication.

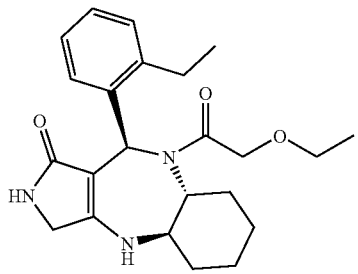

(II)

The compound (II) (100 mg/kg) was orally administered to C57BL/6NCrj mice (11 week age, male) and soon after that, gliclazide (3 mg/kg) was orally administered. After administration, the blood was taken from their caudal veins over time to determine the blood glucose level. Area under the curve of blood glucose level changes until 70 minutes after the administration was set as an index and variations from a control group (Vehicle administered group) were compared.

A remarkable hypoglycemic action was shown in the group in which the compound (II) (100 mg/kg) and gliclazide (3 mg/kg) were administered in combination as compared with a gliclazide (3 mg/kg) alone group and a compound (II) (100 mg/kg) alone group.

Example 2

Investigation of a Combinational Effect with Insulin Secretagogues Using GK Rats The same experiment is conducted as that of Example 1 except that the compounds of the Compound Nos. 6, 8, 62, 80, 81, 88, 91, 98, 105, 106, 129, 130, 131 and 132 in Tables 1 and 2 are used instead of the compound (II), and GK rats are used instead of normal mice. As a result, when the compounds of the Compound Nos. 6, 8, 62, 80, 81, 88, 91, 98, 105, 106, 129, 130, 131 and 132 in Tables 1 and 2 are combined with gliclazide to use, as well as Example 1, a remarkable hypoglycemic action is shown as compared with alone groups.

Example 3

Investigation of a Combinational Effect with Biguanides Using db/db Mice

The compound (III) of the Compound No. 98 in above Table 1, which is indicated by the following structural formula, was used for the investigation. The compound is that described as Example 131 in WO02/44180 and synthesized in accordance with the method described in the international publication.

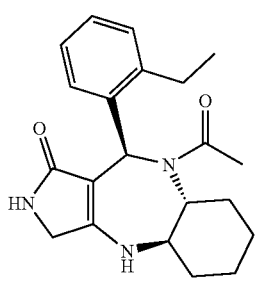

(III)

The compound (III) (30 mg/kg) was orally administered to C57BL/KsJ-db/bdJcl mice (10 week age, male) and soon after that, metformin (100 mg/kg) was orally administered. 60 minutes after administration, the blood was taken from their caudal veins to determine the blood glucose level.

A remarkable hypoglycemic action was shown in the group in which the compound (III) (30 mg/kg) and metformin (100 mg/kg) were administered in combination as compared with a metformin (100 mg/kg) alone group and a compound (III) (30 mg/kg) alone group.

Example 4

Investigation of a Combinational Effect with Biguanides Using KK-Ay Mice

The same experiment is conducted as that of Example 3 except that the compounds of the Compound Nos. 6, 8, 62, 80, 81, 88, 91, 96, 105, 106, 129, 130, 131 and 132 in Tables 1 and 2 are used instead of the compound (III), and KK-Ay mice are used instead of db/bd mice. As a result, when the compounds of the Compound Nos. 6, 8, 62, 80, 81, 88, 91, 96, 105, 106, 129, 130, 131 and 132 in Tables 1 and 2 are combined with metformin to use, as well as Example 3, a remarkable hypoglycemic action is shown as compared with alone groups.

Example 5

Investigation of a Combinational Effect with Glitazones Using db/db Mice (No. 1)

The oral glucose load experiments are conducted using C57BL/KsJ-db/bdJcl mice in the conditions with or without the oral administeration of pioglitazone (10 mg/kg/day) for 10 days and with or without a single oral administration of the compound (III).

A remarkable hypoglycemic action is shown in the group in which the compound (III) and pioglitazone are used in combination as compared with as compared with alone groups.

Example 6

Investigation of a Combinational Effect with Glitazones Using db/db Mice (No. 2)

The same experiment is conducted as that of Example 5 except that the compounds of the Compound Nos. 6, 8, 62, 80, 81, 88, 91, 96, 105, 106, 129, 130, 131 and 132 in Tables 1 and 2 are used instead of the compound (III). As a result, when the compounds of the Compound Nos. 6, 8, 62, 80, 81, 88, 91, 96, 105, 106, 129, 130, 131 and 132 in Tables 1 and 2 are combined with pioglitazone to use, a remarkable hypoglycemic action as well as that in Example 3 is shown as compared with alone groups.

Example 7

Investigation of a Combinational Effect with Insulin Using db/db Mice (No. 1)

The same experiment is conducted as that of Example 3 except that insulin (0.2 U/kg) is used instead of metformin. As a result, when the compound (III) ise combined with insulin to use, a remarkable hypoglycemic action as well as that in Example 3 is shown as compared with alone groups.

Example 8

Investigation of a Combinational Effect with Insulins Using db/db Mice (No. 2)

The same experiment is conducted as that of Example 7 except that the compounds of the Compound Nos. 6, 8, 62, 80, 81, 88, 91, 96, 105, 106, 129, 130, 131 and 132 in Tables 1 and 2 are used instead of the compound (III). As a result, when the compounds of the Compound Nos. 6, 8, 62, 80, 81, 88, 91, 96, 105, 106, 129, 130, 131 and 132 in Tables 1 and 2 are combined with insulin to use, a remarkable hypoglycemic action as well as that in Example 3 is shown as compared with alone groups.

As the above result show, the present invention is useful for treating the diseases caused by hyperglycemia. Namely, when the compound of the formula (I) and at least one kind of an agent selected from above Group A are combined to use, remarkable antidiabetic activity is obtained as compared with the cases in which the compound of the formula (I) or at least one kind of an agent is used by itself. Therefore, the present invention is useful as agents for preventing/treating diabetes, diabetic complication, hyperinsulinemia, disorders of glucose metabolism or obesity.

Since agents for preventing/treating diabetes of the present invention including the combination or mixture of the compound of the formula (I) and at least other one kind of an agent provide the antidiabetic activity, which cannot be obtained by using the conventional hypoglycemic agents, the present invention is highly useful for preventing or treating the diseases caused by hyperglycemia.

The invention claimed is:

1. A pharmaceutical composition comprising a combination of a compound represented by the following formula (I) or pharmaceutically acceptable salts thereof with at least one kind of an agent selected from following Group A:

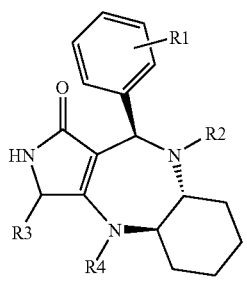
(I)

wherein
$R^1$ is selected from the group consisting of hydrogen, a thioalkyl, a trifluoromethoxy, alkyl, and alkoxyl, or two $R^1$ are present and said R1 are independently an alkyl and a halogen atom,
$R^2$ is a substituted acetyl, and
$R^3$ and $R^4$ are hydrogen;
Group A: gliclazide or metformin.

2. The pharmaceutical composition according to claim 1, wherein the agent of Group A is gliclazide.

3. The pharmaceutical composition according to claim 1, wherein the agent of Group A is metformin.

4. The pharmaceutical composition according to claim 1 whose object is to treat type II diabetes.

5. The pharmaceutical composition of claim 1, wherein said compound of the formula (I) has the following structure:

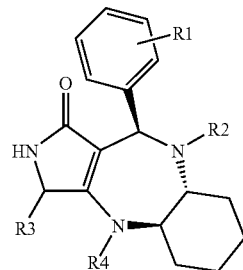

wherein R1 is 2-OMe, R2 is —COCH$_2$CF$_3$, and R3 and R4 are hydrogen; and
wherein said agent of Group A is at least one kind of said agent selected from the group consisting of gliclazide and metformin.

6. The pharmaceutical composition of claim 1, wherein said compound of the formula (I) has the following structure:

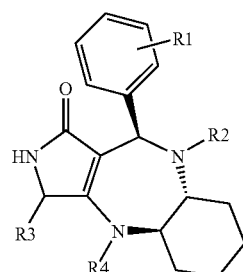

wherein R1 is 2-OMe, R2 is —COCH$_2$OH, and R3 and R4 are hydrogen; and
wherein said agent of Group A is at least one kind of said agent selected from the group consisting of gliclazide and metformin.

7. The pharmaceutical composition of claim 1, wherein said compound of the formula (I) has the following structure:

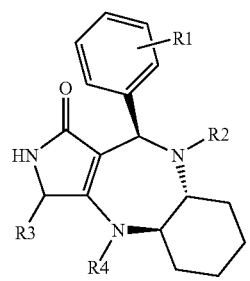

wherein R1 is 2-cyclopropoxy, R2 is —COCH$_2$OH, and R3 and R4 are hydrogen; and
wherein said agent of Group A is at least one kind of said agent selected from the group consisting of gliclazide and metformin.

8. The pharmaceutical composition of claim 1, wherein said compound of the formula (I) has the following structure:

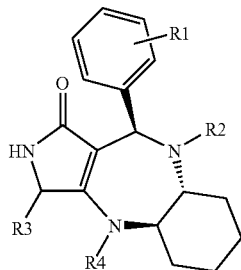

wherein R1 is 2-OCF$_3$, R2 is —COCH$_2$OH, and R3 and R4 are hydrogen; and wherein said agent of Group A is at least one kind of said agent selected from the group consisting of gliclazide and metformin.

9. The pharmaceutical composition of claim 1, wherein said compound of the formula (I) has the following structure:

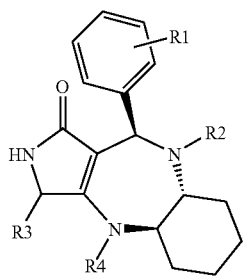

wherein R1 is 2-SMe, R2 is —COCH$_3$, and R3 and R4 are hydrogen; and wherein said agent of Group A is at least one kind of said agent selected from the group consisting of gliclazide and metformin.

10. The pharmaceutical composition of claim 1, wherein said compound of the formula (I) has the following structure:

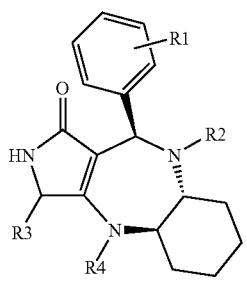

wherein R1 is 2-SMe, R2 is —COCH$_2$OH, and R3 and R4 are hydrogen; and wherein said agent of Group A is at least one kind of said agent selected from the group consisting of gliclazide and metformin.

11. The pharmaceutical composition of claim 1, wherein said compound of the formula (I) has the following structure:

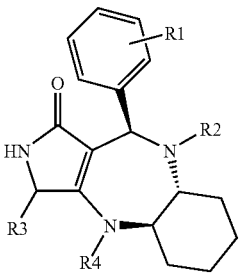

wherein R1 is 2-methyl, R2 is —COCH$_3$, and R3 and R4 are hydrogen; and wherein said agent of Group A is at least one kind of said agent selected from the group consisting of gliclazide and metformin.

12. The pharmaceutical composition of claim 1, wherein said compound of the formula (I) has the following structure:

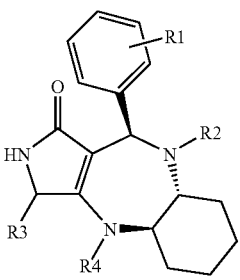

wherein R1 is 2-methyl, R2 is —COCH$_2$CH$_3$, R3 is hydrogen, and R4 is methyl; and wherein said agent of Group A is at least one kind of said agent selected from the group consisting of gliclazide and metformin.

13. The pharmaceutical composition of claim 1, wherein said compound of the formula (I) has the following structure:

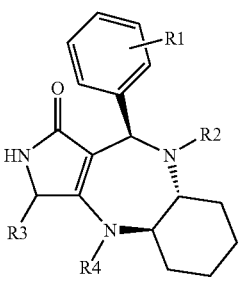

wherein R1 is 2-ethyl, R2 is —COCH$_2$OCH$_2$CH$_3$, and R3 and R4 are hydrogen; and wherein said agent of Group A is at least one kind of said agent selected from the group consisting of gliclazide and metformin.

14. The pharmaceutical composition of claim 1, wherein said compound of the formula (I) has the following structure:

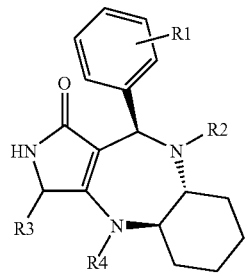

wherein R1 is 2-ethyl, R2 is —COCH₃, and R3 and R4 are hydrogen; and wherein said agent of Group A is at least one kind of said agent selected from the group consisting of gliclazide and metformin.

15. The pharmaceutical composition of claim 1, wherein said compound of the formula (I) has the following structure:

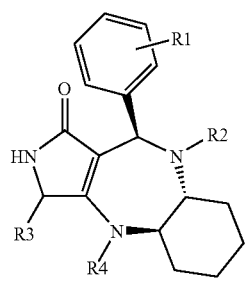

wherein R1 is 2-cyclopropyl, R2 is —COCH₂OH, and R3 and R4 are hydrogen; and wherein said agent of Group A is at least one kind of said agent selected from the group consisting of gliclazide and metformin.

16. The pharmaceutical composition of claim 1, wherein said compound of the formula (I) has the following structure:

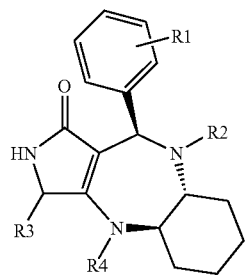

wherein R1 is 2-cyclopropyl, R2 is —COCH₃, and R3 and R4 are hydrogen; and wherein said agent of Group A is at least one kind of said agent selected from the group consisting of gliclazide and metformin.

17. The pharmaceutical composition of claim 1, wherein said compound of the formula (I) has the following structure:

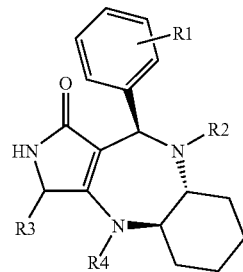

wherein R1 is 2-methyl and 3-fluoro, R2 is —COCH₂CH₃, and R3 and R4 are hydrogen; and wherein said agent of Group A is at least one kind of said agent selected from the group consisting of gliclazide and metformin.

18. The pharmaceutical composition of claim 1, wherein said compound of the formula (I) has the following structure:

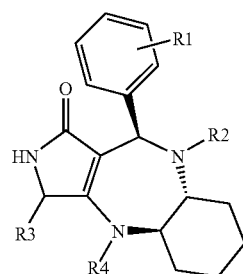

wherein R1, R3, and R4 are hydrogen and R2 is —COCH₃; and wherein said agent of Group A is at least one kind of said agent selected from the group consisting of gliclazide and metformin.

19. The pharmaceutical composition of claim 1, wherein said compound of the formula (I) has the following structure:

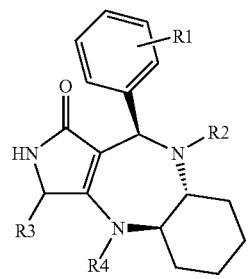

wherein R1, R3, and R4 are hydrogen and R2 is —COCH₂CH₃; and wherein said agent of Group A is at least one kind of said agent selected from the group consisting of gliclazide and metformin.

20. The pharmaceutical composition of claim 1, wherein said compound of the formula (I) has the following structure:

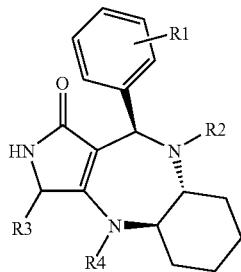

wherein R1, R3, and R4 are hydrogen and R2 is —COCH₂OH; and wherein said agent of Group A is at least one kind of said agent selected from the group consisting of gliclazide and metformin.

21. The pharmaceutical composition of claim 1, wherein said compound of the formula (I) has the following structure:

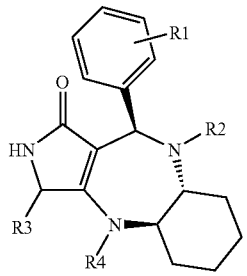

wherein R1, R3, and R4 are hydrogen and R2 is —COCH₂OCH₂CH₃; and wherein said agent of Group A is at least one kind of said agent selected from the group consisting of gliclazide and metformin.

22. A method for treating a type II diabetes comprising administering to a subject in need thereof an effective amount of the pharmaceutical composition according to claim 1.

23. A method for treating type II diabetes comprising administering to a subject in need thereof an effective amount of the pharmaceutical composition according to claim 5.

24. A method for treating a type II diabetes comprising administering to a subject in need thereof an effective amount of the pharmaceutical composition according to claim 6.

25. A method for treating a type II diabetes comprising administering to a subject in need thereof an effective amount of the pharmaceutical composition according to claim 7.

26. A method for treating a type II diabetes comprising administering to a subject in need thereof an effective amount of the pharmaceutical composition according to claim 8.

27. A method for treating a type II diabetes comprising administering to a subject in need thereof an effective amount of the pharmaceutical composition according to claim 9.

28. A method for treating a type II diabetes comprising administering to a subject in need thereof an effective amount of the pharmaceutical composition according to claim 10.

29. A method for treating a type II diabetes comprising administering to a subject in need thereof an effective amount of the pharmaceutical composition according to claim 11.

30. A method for treating a type II diabetes comprising administering to a subject in need thereof an effective amount of the pharmaceutical composition according to claim 12.

31. A method for treating a type II diabetes comprising administering to a subject in need thereof an effective amount of the pharmaceutical composition according to claim 13.

32. A method for treating a type II diabetes comprising administering to a subject in need thereof an effective amount of the pharmaceutical composition according to claim 14.

33. A method for treating a type II diabetes comprising administering to a subject in need thereof an effective amount of the pharmaceutical composition according to claim 15.

34. A method for treating a type II diabetes comprising administering to a subject in need thereof an effective amount of the pharmaceutical composition according to claim 16.

35. A method for treating a type II diabetes comprising administering to a subject in need thereof an effective amount of the pharmaceutical composition according to claim 17.

36. A method for treating a type II diabetes comprising administering to a subject in need thereof an effective amount of the pharmaceutical composition according to claim 18.

37. A method for treating a type II diabetes comprising administering to a subject in need thereof an effective amount of the pharmaceutical composition according to claim 19.

38. A method for treating a type II diabetes comprising administering to a subject in need thereof an effective amount of the pharmaceutical composition according to claim 20.

39. A method for treating a type II diabetes comprising administering to a subject in need thereof an effective amount of the pharmaceutical composition according to claim 21.

* * * * *